US009126949B2

(12) United States Patent
Reddy et al.

(10) Patent No.: US 9,126,949 B2
(45) Date of Patent: Sep. 8, 2015

(54) PROCESS FOR RILPIVIRINE

(75) Inventors: Bandi Parthasaradhi Reddy, Hyderabad (IN); Kura Rathnakar Reddy, Hyderabad (IN); Dasari Muralidhara Reddy, Hyderabad (IN); Adulla Venkat Narsimha Reddy, Hyderabad (IN); Bandi Vamsi Krishna, Hyderabad (IN)

(73) Assignee: HETERO RESEARCH FOUNDATION (IN)

( * ) Notice: Subject to any disclaimer, the term of this patent is extended or adjusted under 35 U.S.C. 154(b) by 0 days.

(21) Appl. No.: 14/113,630

(22) PCT Filed: Feb. 16, 2012

(86) PCT No.: PCT/IN2012/000108
§ 371 (c)(1),
(2), (4) Date: Oct. 24, 2013

(87) PCT Pub. No.: WO2012/147091
PCT Pub. Date: Nov. 1, 2012

(65) Prior Publication Data
US 2014/0228385 A1 Aug. 14, 2014

(30) Foreign Application Priority Data
Apr. 25, 2011 (IN) .......................... 1415/CHE/2011

(51) Int. Cl.
C07D 239/42 (2006.01)
C07D 239/48 (2006.01)
A61K 31/505 (2006.01)
C07C 209/74 (2006.01)

(52) U.S. Cl.
CPC ............ *C07D 239/48* (2013.01); *A61K 31/505* (2013.01); *C07C 209/74* (2013.01); *C07D 239/42* (2013.01)

(58) Field of Classification Search
CPC .......................... C07D 239/42; C07D 239/48
USPC ...................................................... 544/323
See application file for complete search history.

(56) References Cited

U.S. PATENT DOCUMENTS

| 6,197,779 | B1 | 3/2001 | Andries et al. |
| 7,125,879 | B2 | 10/2006 | Guillemont et al. |
| 7,399,856 | B2 | 7/2008 | Schils et al. |
| 7,563,922 | B2 | 7/2009 | Schils et al. |
| 2003/0186990 | A1 | 10/2003 | Kukla et al. |
| 2006/0167253 | A1 | 7/2006 | Schils et al. |
| 2008/0194602 | A1 | 8/2008 | De Kock et al. |
| 2009/0215804 | A1 | 8/2009 | Stevens et al. |
| 2010/0261722 | A1 | 10/2010 | Guillemont et al. |

OTHER PUBLICATIONS

International Search Report and Written Opinion; International Application No. PCT/IN202/000108; International Filing Date Feb. 16, 2012; 8 pages.

*Primary Examiner* — Deepak Rao
(74) *Attorney, Agent, or Firm* — Cantor Colburn LLP

(57) ABSTRACT

The present invention provides a novel process for the preparation of 4-(4-hydroxypyrimidin-2-ylamino)benzonitrile. The present invention also provides a novel process for the preparation of 4-iodo-2,6-dimethyl benzenamine. The present invention further provides an improved process for the preparation of rilpivirine. The present invention further provides a tosylate salt of rilpivirine, process for its preparation and pharmaceutical compositions comprising it.

8 Claims, No Drawings

PROCESS FOR RILPIVIRINE

CROSS-REFERENCE TO RELATED APPLICATIONS

This application is a U.S. national stage of international application No. PCT/IN2012/000108, filed on Feb. 16, 2012, the disclosure of which is incorporated herein by reference in its entirety. Priority is claimed from IN Patent Application No. 1415/CHE/2011, filed Apr. 25, 2011, the disclosure of which is also incorporated herein by reference in its entirety.

FIELD OF THE INVENTION

The present invention provides a novel process for the preparation of 4-(4-hydroxypyrimidin-2-ylamino)benzonitrile. The present invention also provides a novel process for the preparation of 4-iodo-2,6-dimethyl benzenamine. The present invention further provides an improved process for the preparation of rilpivirine. The present invention further provides a tosylate salt of rilpivirine, process for its preparation and pharmaceutical compositions comprising it.

BACKGROUND OF THE INVENTION

Rilpivirine, chemically 4-[[4-[[4-(2-cyanoethenyl)-2,6-dimethylphenyl]amino]pyrimidinyl]amino]benzonitrile and has the structural formula:

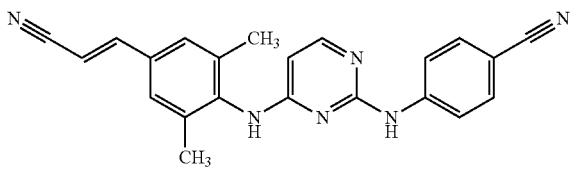 [SMILES: Cc1cc(/C=C/C#N)cc(C)c1Nc1ccnc(Nc2ccc(C#N)cc2)n1]

Rilpivirine (TMC278) is an investigational new drug, developed by Tibotec, for the treatment of HIV infection. It is a second-generation non-nucleoside reverse transcriptase inhibitor (NNRTI) with higher potency, longer half-life and reduced side-effect profile compared with older NNRTIs.

Rilpivirine and its hydrochloride salt were disclosed in U.S. Pat. No. 7,125,879.

Process for the preparation of rilpivirine was disclosed in U.S. Pat. No. 7,399,856 ('856 patent). According to the '856 patent, rilpivirine can be prepared by Scheme I

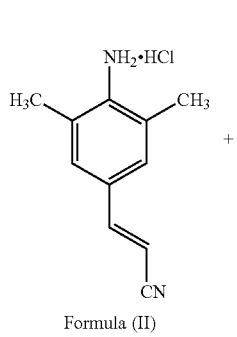

Formula (II)

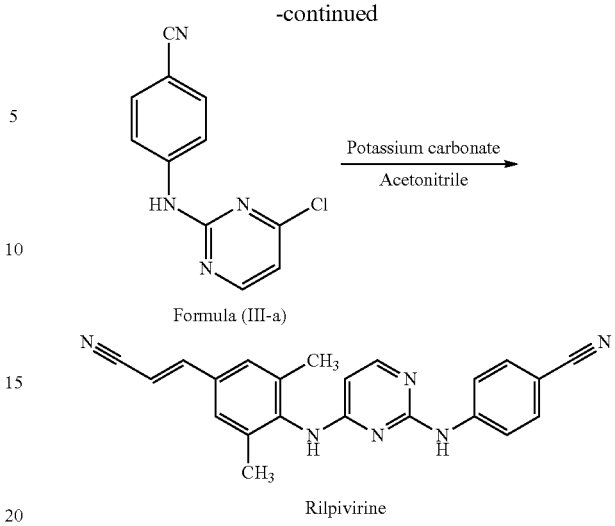

reacting the (E)-3-(4-amino-3,5-dimethylphenyl)acrylonitrile hydrochloride of formula II with 4-(4-chloropyrimidin-2-ylamino)benzonitrile of formula III-a in the presence of potassium carbonate and acetonitrile. The synthetic procedure is illustrated in scheme I, below:

According to the '856 patent described a process for the preparation of 4-(4-chloropyrimidin-2-ylamino)benzonitrile, can be prepared by reacting 4-[(1,4-dihydro-4-oxo-2-pyrimidinyl)amino]benzonitrile with phosphorus oxychloride in presence of sodium hydroxide and methylene chloride.

U.S. Pat. No. 7,563,922 disclosed a process for the preparation of (E)-3-(4-amino-3,5-dimethylphenyl)acrylonitrile hydrochloride.

Fumarate salt of rilpivirine and its process were disclosed in U.S. patent application publication no. 2009/215804.

We have found that a novel process for the preparation of 4-(4-chloropyrimidin-2-ylamino)benzonitrile. 4-(4-Chloropyrimidin-2-ylamino)benzonitrile is a key intermediate for the preparation of rilpivirine.

We have also found that a novel process for the preparation of 4-iodo-2,6-dimethyl benzenamine.

We have also found that an improved process for the preparation of rilpivirine.

The processes of present invention are simple, eco-friendly, inexpensive, reproducible, robust and is well suited on an industrial scale.

We have also found that a tosylate salt of rilpivirine.

Thus, one object of the present invention is to provide a novel process for the preparation of 4-(4-chloropyrimidin-2-ylamino)benzonitrile.

Another object of the present invention is to provide a novel process for the preparation of 4-iodo-2,6-dimethyl benzenamine.

Another object of the present invention is to provide an improved process for the preparation of rilpivirine.

Another object of the present invention is to provide a tosylate salt of rilpivirine, process for its preparation and pharmaceutical compositions comprising it.

The tosylate salt of rilpivirine of the present invention may also serve as intermediate for preparation of rilpivirine and its salts.

SUMMARY OF THE INVENTION

In one aspect, the present invention provides a novel process for the preparation of 4-(4-chloropyrimidin-2-ylamino) benzonitrile of formula I, which comprises:

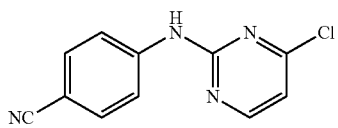
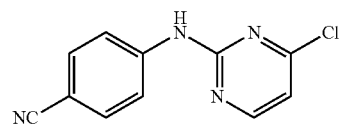

a) condensing the 2-chloro-4-methoxypyrimidine with 4-aminobenzonitrile in the presence of p-toluene sulfonic acid in an ether solvent;

b) reacting the 4-(4-methoxypyrimidin-2ylamino)benzonitrile with pyridine hydrochloride in the presence of a nitrile solvent to obtain 4-(4-hydroxypyrimidin-2ylamino)benzonitrile; and c) reacting the 4-(4-hydroxypyrimidin-2ylamino)benzonitrile with pyridine hydrochloride obtained in step (a) with phosphorous oxychloride in the presence of an alcoholic solvent to obtain a compound of formula I.

In another aspect, the present invention provides a novel process for the preparation of 4-iodo-2,6-dimethyl aniline, which comprises reacting the 2,6-dimethyl aniline with iodine in the presence of a base and a solvent.

In another aspect, the present invention provides an improved process for the preparation of rilpivirine, which comprises:

a) reacting the 4-(4-chloropyrimidin-2-ylamino)benzonitrile with (E)-3-(4-amino-3,5-dimethylphenyl)acrylonitrile hydrochloride in the presence of p-toluene sulfonic acid monohydrate and an ether solvent;

b) heating the contents obtained in step (a) at above 90° C. to obtain a solution;

c) cooling the solution obtained in step (b) at below 35° C.;

d) basifying the solution with a base;

e) extracting rilpivirine into organic solvent;

f) removing the solvent from the solution obtained in step (e) to obtain a solid;

g) slurrying the solid obtained in step (f) with a ketonic solvent, a nitrile solvent or mixture thereof; and h) isolating rilpivirine.

In another aspect, the present invention provides a tosylate salt of rilpivirine.

In another aspect, the present invention provides a process for the preparation of tosylate salt of rilpivirine, which comprises:

a) dissolving rilpivirine in a ketonic solvent;

b) adding p-toluene sulfonic acid to the solution obtained in step (a); and c) isolating tosylate salt of rilpivirine.

Yet in another aspect, the present invention provides a pharmaceutical composition comprising tosylate salt of rilpivirine and pharmaceutically acceptable excipients.

DETAILED DESCRIPTION OF THE INVENTION

The term "room temperature" refers to temperature at about 25 to 35° C.

According to one aspect of the present invention, there is provided a novel process for the preparation of 4-(4-chloropyrimidin-2-ylamino)benzonitrile of formula I, which comprises:

a) condensing the 2-chloro-4-methoxypyrimidine with 4-aminobenzonitrile in the presence of p-toluene sulfonic acid in an ether solvent;

b) reacting the 4-(4-methoxypyrimidin-2ylamino)benzonitrile with pyridine hydrochloride in the presence of a nitrile solvent to obtain 4-(4-hydroxypyrimidin-2ylamino)benzonitrile; and c) reacting the 4-(4-hydroxypyrimidin-2ylamino)benzonitrile with pyridine hydrochloride obtained in step (a) with phosphorous oxychloride in the presence of an alcoholic solvent to obtain a compound of formula I.

The ether solvent used in step (a) may preferably be a solvent or mixture of solvents selected from tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane and methoxyethane, and more preferably ether solvent is 1,4-dioxane.

Preferably the nitrile solvent used in step (b) may be a solvent or mixture of solvents selected from acetonitrile, propionitrile, butyronitrile and benzonitrile. More preferably the nitrile solvent is acetonitrile.

The alcoholic solvent used in step (c) may preferably be a solvent or mixture of solvents selected from methanol, ethanol, isopropyl alcohol, tert-butyl alcohol, n-butanol and isobutyl alcohol, and more preferably the alcoholic solvent is isopropyl alcohol.

According to another aspect of the present invention, there is provided a novel process for the preparation of 4-iodo-2,6-dimethyl aniline, which comprises reacting the 2,6-dimethyl aniline with iodine in the presence of a base and a solvent.

The solvent used in the process may preferably be a solvent or mixture of solvents selected from tetrahydrofuran, 1,4-dioxane, methyl tert-butyl ether, diisopropyl ether and diethyl ether. More preferably the solvent is 1,4-dioxane.

The base used in the process may preferably be selected from pyridine, N-methylpyrrolidone or dimethylacetamide.

According to another aspect of the present invention, there is provided an improved process for the preparation of rilpivirine, which comprises:

a) reacting the 4-(4-chloropyrimidin-2-ylamino)benzonitrile with (E)-3-(4-amino-3,5-dimethylphenyl)acrylonitrile hydrochloride in the presence of p-toluene sulfonic acid monohydrate and an ether solvent;

b) heating the contents obtained in step (a) at above 90° C. to obtain a solution;

c) cooling the solution obtained in step (b) at below 35° C.;

d) basifying the solution with a base;

e) extracting rilpivirine into organic solvent;

f) removing the solvent from the solution obtained in step (e) to obtain a solid;

g) slurrying the solid obtained in step (f) with a ketonic solvent, a nitrile solvent or mixture thereof; and h) isolating rilpivirine.

The ether solvent used in step (a) may preferably be a solvent or mixture of solvents selected from tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane and methoxyethane, and more preferably ether solvent is 1,4-dioxane.

The reaction in step (b) may preferably be heated to 100 to 110° C.

Step (c) may preferably be carried out at room temperature.

The base used in step (d) may preferably be selected from alkali metal hydroxides, alkali metal carbonates or alkali metal bicarbonates. More preferably the base is sodium bicarbonate or potassium bicarbonate.

The organic solvent used in step (e) may preferably be a solvent or mixture of solvents selected from methylene chloride, chloroform, carbon tetrachloride, ethylene dichloride, ethyl acetate, methyl acetate, isopropyl acetate, tert-butyl methyl acetate and ethyl formate. More preferably the organic solvents are methylene chloride and ethyl acetate.

Removal of the solvent in step (f) may be carried out at atmospheric pressure or at reduced pressure. Removal of the solvent may preferably be carried out until the solvent is almost completely distilled off.

The ketonic solvent and nitrile solvent used in step (g) may preferably be selected from acetone, methyl ethyl ketone, methyl isobutyl ketone, diethyl ketone, acetonitrile, propionitrile, butyronitrile and benzonitrile. More preferably the solvents are acetone and acetonitrile.

Rilpivirine may be isolated in step (h) by the methods known such as filtration or centrifugation.

According to another aspect of the present invention, there is provided a tosylate salt of rilpivirine.

According to another aspect of the present invention, there is provided a process for the preparation of tosylate salt of rilpivirine, which comprises:

a) dissolving rilpivirine in a ketonic solvent;
b) adding p-toluene sulfonic acid to the solution obtained in step (a); and
c) isolating tosylate salt of rilpivirine.

The ketonic solvent used in step (a) may preferably be selected from acetone, methyl ethyl ketone, methyl isobutyl ketone and diethyl ketone, and more preferably the ketonic solvent is acetone.

The p-toluene sulfonic acid used in step (b) can be added directly or as a solution with a solvent. Preferably the solvent is acetone.

Isolation of tosylate salt of rilpivirine in step (c) may preferably be performed by conventional techniques such as centrifugation and filtration.

According to another aspect of the present invention, there is provided a pharmaceutical composition comprising tosylate salt of rilpivirine and pharmaceutically acceptable excipients, and optionally other therapeutic ingredients. The tosylate salt of rilpivirine may preferably be formulated into tablets, capsules, suspensions, dispersions, injectables or other pharmaceutical forms.

The invention will now be further described by the following examples, which are illustrative rather than limiting.

PREPARATIVE EXAMPLES

Preparative Example 1

Preparation of 2,4-dichloro pyrimidine

To a mixture of N,N-dimethyl aniline (140 gm) and uracil (100 gm) was added phosphorous oxychloride (342 gm) slowly at 0° C. The contents were then heated to reflux and maintained for 4 hours. The solution was then cooled to room temperature, then transferred in to ice water and stirred for 1 hour. The resulting precipitate was filtered and washed with water. The solid thus obtained was recrystallized from hexane to give 80 gm of 2,4-dichloro pyrimidine.

Preparative Example 2

Preparation of 2-chloro-4-methoxypyrimidine

To a solution of 2,4-dichloro pyrimidine (20 gm) in methanol (200 ml) was added sodium methoxide (8.7 gm) at 0 to 5° C. The resulting mixture was stirred for 14 hours at room temperature and then concentrated under reduced pressure to obtain a residual mass. The residual mass obtained was extracted with ethyl acetate and water. The combined organic layers were washed with water and sodium chloride solution, and then concentrated under vacuum to obtain a crude solid. The crude solid obtained was dissolved in hexane (40 ml) at 0 to 5° C. and stirred for 1 hour. The solid obtained was collected by filtration and then dried to obtain 9.7 gm of 2-chloro-4-methoxypyrimidine.

EXAMPLES

Example 1

Preparation of 4-(4-methoxypyrimidin-2-ylamino)benzonitrile 1,4-Dioxane (100 ml) was added to a mixture of 2-chloro-4-methoxypyrimidine (20 gm) as obtained in preparative example 2, 4-aminobenzonitrile (16.33 gm) and p-toluene sulfonic acid (42.12 gm). The mixture was then heated to 100 to 110° C. and stirred for 14 hours. The solution was then cooled to room temperature and basified with saturated sodium bicarbonate solution. The layers were separated and the aqueous layer was extracted with ethyl acetate. The combined organic layers were washed with water and then concentrated to obtain a residual solid. The residual solid obtained was slurried in isopropyl alcohol at room temperature for 30 minutes and filtered. The solid obtained was then dried to give 17.3 gm of 4-(4-methoxypyrimidin-2-ylamino) benzonitrile.

Example 2

Preparation of 4-(4-hydroxypyrimidin-2-ylamino)benzonitrile

Pyridine hydrochloride (23 gm) was added to 4-(4-methoxypyrimidin-2-ylamino)benzonitrile (15 gm) and then heated to 150 to 160° C. for 3 hours. The mixture was then cooled to room temperature, then transferred in to ice water and stirred for 1 hour. The resulting precipitate was filtered and washed with water. The solid thus obtained was slurried in acetonitrile at 0 to 5° C. for 1 hour and filtered. The solid obtained was dried to give 12.3 gm of 4-(4-hydroxypyrimidin-2-ylamino)benzonitrile.

Example 3

Preparation of 4-(4-chloropyrimidin-2-ylamino)benzonitrile

Phosphorous oxychloride (104 gm) was added slowly to 4-(4-hydroxypyrimidin-2-ylamino)benzonitrile (12 gm) at 0° C. and then heated to reflux for 1 hour. The solution was then cooled to room temperature, stirred for 30 minutes and filtered. The precipitated solid thus obtained was dissolved in isopropyl alcohol at 0 to 5° C. and stirred for 1 hour at 0 to 5° C. The solid obtained was collected by filtration and then dried to obtain 9.75 gm of 4-(4-chloropyrimidin-2-ylamino) benzonitrile.

Example 4

Preparation of 4-iodo-2,6-dimethyl benzenamine

To a solution of 2,6-dimethyl aniline (50 gm) in 1,4-dioxane (400 ml) and pyridine (40 ml) was added iodine (157.3 gm) slowly at 0° C. The solution was stirred for 1 hour at 0° C. and the temperature was raised to room temperature. The solution was stirred for 1 hour at room temperature and then added a saturated solution of sodium thiosulfate. The layers were separated and the aqueous layer was extracted with methylene chloride. The combined organic layers were dried with anhydrous sodium sulfate and the solvent was evaporated in vacuum to obtain 91.8 gm of 4-iodo-2,6-dimethyl benzenamine.

Example 5

Preparation of 4-iodo-2,6-dimethyl benzenamine

To a solution of 2,6-dimethyl aniline (50 gm) in 1,4-dioxane (400 ml) and N-methylpyrrolidone (40 ml) was added iodine (157.3 gm) slowly at 0° C. The solution was stirred for 1 hour at 0° C. and the temperature was raised to room temperature. The solution was stirred for 1 hour at room temperature and then added a saturated solution of sodium thiosulfate. The layers were separated and the aqueous layer was extracted with methylene chloride. The combined organic layers were dried with anhydrous sodium sulfate and the solvent was evaporated in vacuum to obtain 91 gm of 4-iodo-2,6-dimethyl benzenamine.

Example 6

Preparation of 4-iodo-2,6-dimethyl benzenamine

To a solution of 2,6-dimethyl aniline (25 gm) in 1,4-dioxane (200 ml) and dimethylacetamide (20 ml) was added iodine (79 gm) slowly at 0° C. The solution was stirred for 1 hour at 0° C. and the temperature was raised to room temperature. The solution was stirred for 1 hour at room temperature and then added a saturated solution of sodium thiosulfate. The layers were separated and the aqueous layer was extracted with methylene chloride. The combined organic layers were dried with anhydrous sodium sulfate and the solvent was evaporated in vacuum to obtain 45 gm of 4-iodo-2,6-dimethyl benzenamine.

Example 7

Preparation of (E)-3-(4-amino-3,5-dimethylphenyl)acrylonitrile hydrochloride

Sodium acetate (13.27 gm), palladium on charcoal (0.858 gm) and dimethylacetamide (400 ml) were added and then heated to 140° C. under nitrogen atmosphere. A solution of 4-iodo-2,6-dimethyl benzenamine (20 gm), acrylonitrile (10.72 ml) and dimethylacetamide (200 ml) was added slowly to the reaction mixture. The reaction mixture was maintained for 12 hours at 140° C. The reaction mass was then cooled to room temperature and filtered through celite. The filtrate obtained was treated with water and then the layers were separated. The aqueous layer was extracted with ethyl acetate and the combined organic layers were washed with water and sodium chloride solution. The organic layer was dried with sodium sulfate and the solvent was evaporated in vacuum to obtain crude oily residue.

To the crude oily residue obtained above was added ethanol (210 ml). The solution was then heated to 60° C. and then added a solution hydrochloride in isopropyl alcohol (69.5 ml). The reaction mixture was stirred for 1 hour at 60° C. and then cooled to room temperature. The solid obtained was collected by filtration and then dried to obtain 11.5 gm of (E)-3-(4-amino-3,5-dimethylphenyl)acrylonitrile hydrochloride.

Example 8

Preparation of Rilpivirine

To a mixture of 4-(4-chloropyrimidin-2-ylamino)benzonitrile (4.5 gm) as obtained in example 3, (E)-3-(4-amino-3,5-dimethylphenyl)acrylonitrile hydrochloride (4.07 gm) as obtained in example 7 and p-toluenesulfonic acid monohydrate (4.45 gm) was added 1,4-dioxane (90 ml) under stirring. The mixture was then heated to 100 to 110° C. and stirred for 14 hours. The solution was then cooled to room temperature and then added saturated sodium bicarbonate solution. The layers were separated and the aqueous layer was extracted with ethyl acetate. The combined organic layers were dried with sodium sulfate and then concentrated to obtain a crude solid.

The crude solid obtained above was dissolved in acetone and stirred for 1 hour at room temperature. The separated solid was filtered and then dried to obtain 4 gm of rilpivirine.

Example 9

Preparation of Rilpivirine

Example 8 was repeated using acetonitrile solvent instead of acetone solvent to obtain rilpivirine.

Example 10

Preparation of Rilpivirine Hydrochloride

Rilpivirine (1.3 gm) as obtained in example 8 was dissolved in a mixture of methanol and methylene chloride (1:2; 72 ml). To the solution was passed dry hydrochloride gas until the precipitation obtained. The reaction mixture was stirred for 1 hour at 0° C. and filtered. The solid obtained was dried to give 0.8 gm of rilpivirine hydrochloride.

Example 11

Preparation of Tosylate Salt of Rilpivirine

Rilpivirine (1 gm) was dissolved in acetone (50 ml) and then added a solution of p-toluene sulfonic acid (0.4 gm) in acetone (20 ml). The reaction mass was stirred for 1 hour at room temperature and filtered. The solid obtained was dried to give 1 gm of to sylate salt of rilpivirine.

We claim:
1. A process for the preparation of rilpivirine, which comprises:

a. reacting the 4-(4-chloropyrimidin-2-ylamino)benzonitrile with (E)-3-(4-amino-3,5-dimethylphenyl)acrylonitrile hydrochloride in the presence of p-toluene sulfonic acid monohydrate and an ether solvent;
b. heating the contents obtained in step (a) at above 90° C. to obtain a solution;
c. cooling the solution obtained in step (b) at below 35° C.;
d. basifying the solution with a base;
e. extracting rilpivirine into organic solvent;
f. removing the solvent from the solution obtained in step (e) to obtain a solid;
g. slurrying the solid obtained in step (f) with a ketonic solvent, a nitrile solvent or mixture thereof; and
h. isolating rilpivirine.

2. The process as claimed in claim 1, wherein the ether solvent used in step (a) is a solvent or mixture of solvents selected from tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane and methoxyethane.

3. The process as claimed in claim 2, wherein the ether solvent is 1,4-dioxane.

4. The process as claimed in claim 1, wherein the base used in step (d) is selected from sodium bicarbonate or potassium bicarbonate.

5. The process as claimed in claim 1, wherein the organic solvent used in step (e) is a solvent or mixture of solvents selected from methylene chloride, chloroform, carbon tetrachloride, ethylene dichloride, ethyl acetate, methyl acetate, isopropyl acetate, tert-butyl methyl acetate and ethyl formate.

6. The process as claimed in claim 5, wherein the organic solvents are methylene chloride and ethyl acetate.

7. The process as claimed in claim 1, wherein the ketonic solvent and nitrile solvent used in step (g) are selected from acetone, methyl ethyl ketone, methyl isobutyl ketone, diethyl ketone, acetonitrile, propionitrile, butyronitrile and benzonitrile.

8. The process as claimed in claim 7, wherein the solvents are acetone and acetonitrile.

* * * * *